United States Patent [19]

Shiraishi et al.

[11] 3,968,166
[45] July 6, 1976

[54] CATALYTIC PROCESS FOR THE PREPARATION OF ACROLEIN

[75] Inventors: Tatsuo Shiraishi; Susumu Kishiwada; Shinkichi Shimizu; Shigeru Honmaru, all of Niihama; Akihiko Atsumi, Funabashi; Hiroshi Ichihashi; Yoshihiko Nagaoka, both of Niihama, all of Japan

[73] Assignee: Sumitomo Chemical Company, Limited, Japan

[22] Filed: May 30, 1975

[21] Appl. No.: 582,077

Related U.S. Application Data

[63] Continuation-in-part of Ser. No. 262,489, June 14, 1972, abandoned.

[30] Foreign Application Priority Data

June 14, 1971  Japan.................. 46-42310

[52] U.S. Cl.............................. 260/604 R; 252/426
[51] Int. Cl.²......................................... C07C 45/04
[58] Field of Search.................. 260/604 R; 262/489

[56] References Cited
UNITED STATES PATENTS 3,454,630  7/1969  Yamaguchi et al............. 260/604 R Primary Examiner—James O. Thomas, Jr.
Assistant Examiner—W. B. Lone
Attorney, Agent, or Firm—Stewart and Kolasch, Ltd.

[57] ABSTRACT

A process for the preparation of acrolein by the vapor phase catalytic oxidation of propylene which comprises contacting propylene and oxygen with a catalyst composition comprising a catalyst system of the formula:

$$Mo_aBi_bFe_cNi_dTl_eP_fX_gY_hO_i$$

wherein X is one or more of Mg, Mn and Co, Y is one or more of Cu, Ca, Sr, Zn, Cd, Sn and Pb and $a$, $b$, $c$, $d$, $e$, $f$, $g$, $h$ and $i$ represent respectively the number of atoms and, when $a$ is 12, $b$ is 0.1 to 5, $c$ is 0.1 to 12, $d$ is 0.1 to 12, $e$ is 1 or less but not 0, $f$ is 0 to 5, $g$ is 0 to 12, $h$ is 0.1 to 12 and $i$ is a number determined by the valence requirements of the other atoms present and from 36.5 to 95.8, provided that $b$ plus $c$ is from 0.2 to 12.5 and $d$ plus $g$ plus $h$ is from 0.2 to 27. The process can provide acrolein in a high selectivity and an excellent single pass yield even at a large space velocity of the propylene feed.

16 Claims, 1 Drawing Figure

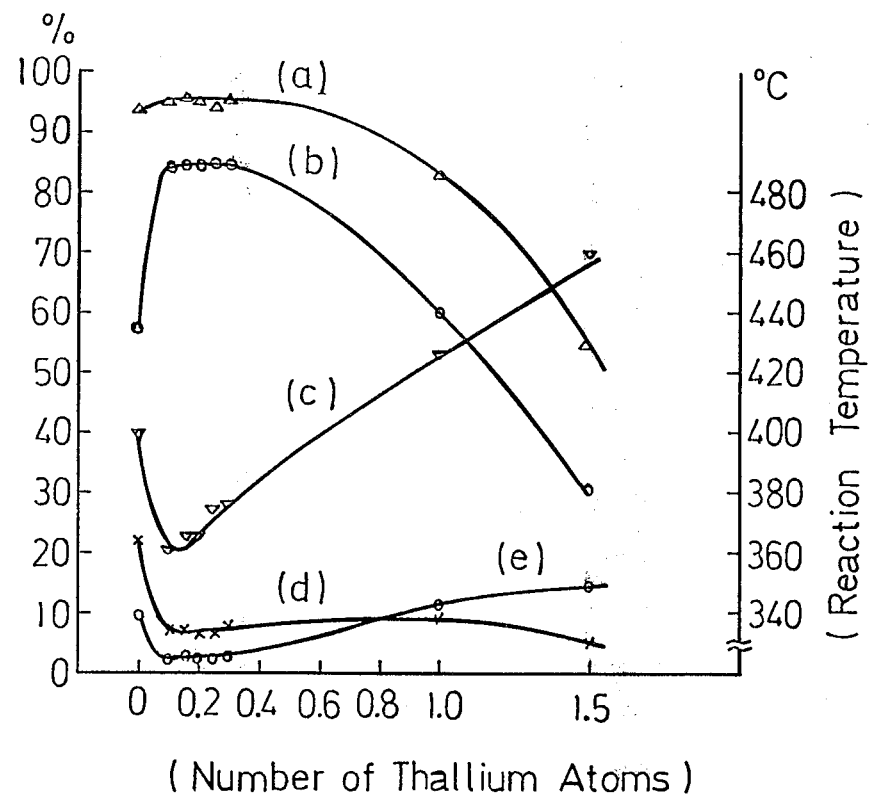

CATALYTIC PROCESS FOR THE PREPARATION OF ACROLEIN

This application is a continuation-in-part application of Ser. No. 262,489 filed June 14, 1972 now abandoned.

The present invention relates to a catalytic process for the preparation of acrolein. More particularly, it relates to a process for the preparation of acrolein by the catalytic vapor phase oxidation of propylene with oxygen in the presence of a specific catalyst system.

It is generally known that, in the vapor phase catalytic oxidation of olefinic hydrocarbons to the corresponding unsaturated aldehydes, the selection of an appropriate catalyst and suitable reaction conditions is essential for providing a high conversion and excellent selectivity of the starting olefinic hydrocarbon to the objective unsaturated aldehyde under such a condition that the starting material is fed at a large space velocity. In the production of acrolein from propylene, however, the elevation of reaction temperatures to attain a higher conversion of propylene may usually cause a marked depression of selectivity of propylene to acrolein. From this reason, conventional catalyst compositions require propylene to be fed at a low space velocity and a low reaction temperature in order to achieve a high yield of acrolein.

A variety of catalyst compositions has heretofore been proposed for the vapor phase oxidation of olefinic hydrocarbons to the corresponding unsaturated aldehydes which comprise multi-elements in the oxide form. Of these, a catalyst system comprising Mo, Bi, P, at least one of Fe, Co and Ni and O is particularly well known in view of the excellent conversion of the starting olefinic hydrocarbons [U.S. Pat. No. 3,454,630; German Pat. No. 1,268,609; French Pat. No. 1,514,167; Japanese Pat. Publication No. 2,324/1968; Japanese Pat. Publication No. 5,855/1969 and Japanese Pat. Publication No. 6,245/1969]. When such catalyst compositions are applied to the vapor phase oxidation of propylene to acrolein, a high conversion of propylene and a high selectivity to acrolein may be attained simultaneously if the propylene is fed at a relatively low space velocity. When the space velocity becomes higher, however, a selectivity to acrolein may be remarkably decreased. Thus, these particular catalyst compositions are disadvantageous in essentially requiring a low space velocity of the propylene feed for attaining a high yield.

Furthermore, the use of conventional catalyst compositions in the oxidation of olefinic hydrocarbons with high space velocities at elevated temperatures to increase the conversion of the olefinic hydrocarbons may cause the by-production of large amounts of carbon monoxide, carbon dioxide and the like with marked generation of heat, whereby the control of the reaction conditions is made difficult.

In the course of studies seeking a catalyst composition which can provide a favorable catalytic activity, it has previously been found that a catalyst system comprising Mo, Bi, Fe, Ni, Tl, P and O could overcome the disadvantages as prevailing in conventional catalyst compositions. Thus, such a catalyst system can convert propylene to acrolein in a high conversion and an excellent selectivity even at a high space velocity. In addition, the catalyst system has advantages in suppressing markedly the production of by-products such as carbon monoxide, carbon dioxide and acrylic acid. This catalyst, however, is not satisfactory in its catalytic life.

As the result of further studies, it has now been found that a catalyst system in which two groups of elements are added to the said catalyst system comprising Mo, Bi, Fe, Ni, Tl, P and O, one of said groups being at least one of Mg, Mn and Co and the other group being at least one of Cu, Ca, Sr, Zn, Cd, Sn and Pb, can exhibit a more favorable catalytic activity in the conversion of propylene into acrolein than the said catalyst system containing no such additional elements. That is, the former can afford acrolein from propylene in a higher conversion and a more excellent selectivity with a longer catalytic life than the latter.

The process of the present invention comprises contacting propylene and oxygen with a catalyst composition comprising a catalyst system of the formula:

$$Mo_aBi_bFe_cNi_dTl_eP_fX_gY_hO_i$$

wherein X is a member or a combination of members selected from the group consisting of Mg, Mn and Co, Y is a member or a combination of members selected from the group consisting of Cu, Ca, Sr, Zn, Cd, Sn and Pb and $a$, $b$, $c$, $d$, $e$, $f$, $g$, $h$ and $i$ represent respectively the number of atoms, and, when $a$ is 12, $b$ is from 0.1 to 5, $c$ is from 0.1 to 12, $d$ is from 0.1 to 12, $e$ is 1 or less but not 0, $f$ is from 0 to 5, $g$ is from 0 to 12, $h$ is from 0.1 to 12 and $i$ is a number determined by the valence requirements of the other atoms present and from 36.5 to 95.8, provided that $b$ plus $c$ is from 0.2 to 12.5 and $d$ plus $g$ plus $h$ is from 0.2 to 27; preferably, when $a$ is 12, $b$ is from 0.1 to 5, $c$ is from 0.1 to 7.5, $d$ is from 0.1 to 12, $e$ is from 0.05 to 1, $f$ is up to 2, $g$ is up to 9, $h$ is from 0.1 to 6 and $i$ is from 36.4 to 77.0; and, more preferably, when $a$ is 12, $b$ is from 0.1 to 5, $c$ is from 0.1 to 7.5, $d$ is from 0.1 to 12, $e$ is from 0.05 to 1, $f$ is up to 2, $g$ is up to 9, $h$ is from 0.1 to 6 and $i$ is from 42.8 to 70.5, provided that $b$ plus $c$ is from 0.5 to 10 and $d$ plus $g$ plus $h$ is from 6 to 13. In the foregoing definition, the component X is preferably any single element or any combination of up to two different kinds of said elements; and the component Y is preferably any single element or any combination of up to two different kinds of said elements and the element of the component Y is preferably Cu, Zn, Cd or Sn or a combination thereof and, more preferably, Zn. It should be noted, however, that any combination of more than two different elements of the component X or Y be construed as being encompassed within the scope of the present invention.

The starting materials to be used for the vapor phase oxidation of this invention are propylene and oxygen. As the oxygen source, there may be used pure oxygen gas, air enhanced or unenhanced in oxygen concentrations or any other oxygen-containing gas. From the economical viewpoint, the use of air is preferred. Although acrolein can be prepared from propylene in high yield without steam, the presence of steam in the starting gas mixture is desired for the ease of removal of heat generated and from the point of view of catalyst life. It should be noted, however, that the reaction without using steam be construed as being an embodiment and feature of the present carrying When the low molar ratio of propylene to oxygen of 1 : 0.5, for example, is employed, there may be cases where the conversion of propylene may not be increased because of the lack of oxygen present. In this case, however, an extremely high selectivity to acrolein from the propylene can be achieved. Accordingly, said range is satisfactory in carring out the process of the present invention although the ratio of propylene to oxygen of 1 : 1 to 1 : 3 may be preferable from the economic point of view. When steam is introduced, it may be used in a molar ratio to propylene of about 1 : 1 to 15 : 1, preferably 3 : 1 to 10 : 1. If desired, an appropriate inert gas such as nitrogen, carbon dioxide or argon may be used as a diluent.

The catalyst system of the present invention may be prepared employing molybdenum compounds (e.g., ammonium molybdate, molybdenum oxide or molybdic acid), bismuth compounds (e.g., bismuth nitrate or bismuth oxide), iron compounds (e.g., iron nitrate or iron oxide), nickel compounds (e.g., nickel nitrate or nickel oxide), manganese compounds (e.g., manganese nitrate or manganese oxide), magnesium compounds (e.g., magnesium nitrate or magnesium oxide), cobalt compounds (e.g., cobalt nitrate or cobalt oxide), copper compounds (e.g., copper nitrate or copper oxide), calcium compounds (e.g., calcium nitrate or calcium oxide), strontium compounds (e.g., strontium nitrate or strontium oxide), zinc compounds (e.g., zinc nitrate or zinc oxide), cadmium compounds (e.g., cadmium nitrate or cadmium oxide), lead compounds (e.g., lead nitrate or lead oxide), tin compounds (e.g, tin chloride or tin oxide), thallium compounds (e.g., thallium nitrate, thallium oxide or thallium phosphate) and phosphorus compounds (e.g., phosphoric acid or ammonium phosphate).

The catalyst composition of the present invention may be prepared by a per se conventional process. For instance, a bismuth salt, an iron salt, a nickel salt, a manganese salt, a magnesium salt, a cobalt salt, a copper salt, a calcium salt, a strontium salt, a zinc salt, a cadmium salt, a tin salt, a lead salt, a thallium salt and/or a phosphorus compound are added to an aqueous solution of a molybdate such as ammonium molybdate, and the resulting slurry is admixed with a carrier material and evaporated to dryness. The resultant cake is then calcined at an elevated temperature in the atmosphere and, after cooling, crushed and shaped into pellets or granules.

The catalyst system of the present invention may be used as such, but it is favorably incorporated with a suitable carrier (e.g., sillica, alumina, silicon carbide or titanium oxide). The amount of the carrier may vary with its kind and may be usually less than 90 % by weight, preferably from 5 to 90 % by weight, of the catalyst composition.

The production of acrolein using the catalyst composition of the present invention may be carried out by the fluidized bed or fixed bed process. The particle size of the catalyst composition is not particularly limited and may optionally be varied with the type of its application. The reaction temperature is associated with the kind of the catalyst composition and is usually from 200° to 550° C. preferably from 250° to 500° C. and, more preferably, from 300° to 450° C. The reaction pressure may be around atmospheric pressure, preferably from 0.7 to 5 absolute atmospheres. The space velocity is ordinarily from 100 to 24,000, preferably from 200 to 12,000 and, more preferably, from 300 to 8,000, liter-gas per liter-catalyst per hour.

The catalyst composition comprising Mo, Bi, Fe, Ni, Tl, P and O can yield acrolein from propylene with a desirable conversion of propylene and an excellent selectivity to acrolein even at a great space velocity and a low reaction temperature. However, when the incorporation of at least one, preferably up to two, of Cu, Ca, Sr, Zn, Cd, Sn and Pb and at least one, preferably up to two, of Mg, Mn and Co, into said catalyst composition of the present invention is made according to the present invention, the resulting catalyst composition is advantageous in attaining a higher conversion of propylene and a more excellent selectivity to acrolein with a marked suppression of the production of by-products such as acrylic acid, carbon monoxide and carbon dioxide at a lower reaction temperature. Particularly notable is the extreme prolongation of the catalytic life of the catalyst composition to be used for the present invention. For instance, even after a 50-day continuous oxidation reaction, the catalyst composition of this invention shows no material depression in the acrolein yield (e.g., 84.2 percent at the initial stage and 84.5 percent at the finish stage).

Moreover, the catalyst composition of the present invention is characterized by the presence of a small amount of thallium. As compared with the corresponding catalyst system which, however, does not contain Tl, the Tl-containing catalyst system can provide a remarkably higher conversion of propylene and suppress markedly the by-production of carbon monoxide, carbon dioxide and the like so that the selectivity to acrolein is highly increased. Attention is directed, however, to the fact that the incorporation of thallium in excess may rather cause to interfer with or impair the production of acrolein. From these facts, it may be assumed that the catalytic mechanism of the Tl-containing catalyst system is different from that of the catalyst system not containing Tl and that the thallium component in the Tl-containing catalyst system is present not in a mere oxide form, but in a certain complex compound form. The said assumption may be supported by the fact that, while thallium oxide is apt to be reduced in a reductive atmosphere to the lower oxide form or metallic thallium of high volatility, the Tl-containing catalyst system does not materially lose its catalytic activity even after its use in a continuous oxidation for 50 days, for example, and the non-volatilization of the thallium component present therein is confirmed by the fluorescent X-ray analysis.

The following examples illustrate the present invention without, however, limiting the same thereto. In the following examples, the conversion of propylene, the selectivity to acrolein, the yield of acrolein and the space velocity are calculated, respectively, according to the formulas:

$$\text{Conversion of propylene (\%)} = \frac{\text{Reacted propylene (mol)}}{\text{Feed propylene (mol)}} \times 100$$

$$\text{Selectivity of acrolein (\%)} = \frac{\text{Produced acrolein (mol)}}{\text{Reacted propylene (mol)}} \times 100$$

$$\text{Yield of acrolein (\%)} = \frac{\text{Produced acrolein (mol)}}{\text{Feed propylene (mol)}} \times 100$$

$$\text{Space velocity} = \frac{\text{Flow volume of feed gas (liter/hour)}}{\text{Volume of catalyst (liter)}}$$

EXAMPLE 1

In a solution of 12.13 g. of bismuth nitrate in a mixture of 4 ml. of concentrated nitric acid and 30 ml. of water was combined with a solution of 20.20 g. of ferric nitrate, 14.86 g. of zinc nitrate, 47.34 g. of nickel nitrate and 0.67 g. of thallium in 250 ml. of water. To the resultant mixture was added a solution of 52.98 g. of ammonium molybdate and 0.29 g. of concentrated phosphoric acid (85 % by weight) in a mixture of 30 ml. of an ammonia aqueous solution (28 % by weight) and 300 ml. of water, and the resulting mixture was stirred well to make a slurry dispersion. To this dispersion was added 100 ml. of silica sol ($SiO_2$, 20 % by weight) while being vigorously stirred. The resultant slurry dispersion was evaporated to dryness, and the residue was calcined at 300°C. for 3 hours (1st calcination), cooled and crushed. The resulting powder was tabletted and calcined at 525° C. for 6 hours in the atmosphere (2nd calcination) to give a catalyst composition having the following formula:

$Mo_{12}Bi_1Fe_2Ni_{6.5}Tl_{0.1}P_{0.1}Zn_2O_{49.4}$ (wherein the carrier component is omitted).

Said catalyst composition in granules of 10 to 16 mesh (8.0 ml.) was charged into a glass reaction tube of 12 mm. in inner diameter and heated. A gaseous mixture of propylene, air and steam (molar ratio, 1 : 7 : 7) was introduced into the reaction tube at 350° C. and at a space velocity of 1,200 liter-gas/liter-catalyst/hour, whereby acrolein was produced. The conversion of propylene was 94.3 %, the selectivity to acrolein was 90.2 %. The yields of acrolein, acrylic acid, acetic acid, acetaldehyde, carbon dioxide and carbon monoxide were, respectively, 84.8 %, 5.8 %, 0.7 %, 0.3 %, 1.5 % and 0.8 %. The space time yield of acrolein was 3.03 mole/liter-catalyst/hour.

EXAMPLE 2

The process of Example 1 was repeated using the procedure and reagents used therein to give a catalyst system of the formula:

$Mo_{12}Bi_1Fe_2Ni_6Tl_eP_{0.1}Zn_3O_h$ wherein $e$ is 0 to 1.5 and $h$ is 49.8 to 52.0. The catalyst system prepared have the following specific formulas:

| Catalyst system Number | Formula |
|---|---|
| I | $Mo_{12}Bi_1Fe_2Ni_6P_{0.1}Zn_3O_{49.8}$ |
| II | $Mo_{12}Bi_1Fe_2Ni_6Tl_{0.1}P_{0.1}Zn_3O_{49.9}$ |
| III | $Mo_{12}Bi_1Fe_2Ni_6Tl_{0.15}P_{0.1}Zn_3O_{50.0}$ |
| IV | $Mo_{12}Bi_1Fe_2Ni_6Tl_{0.2}P_{0.1}Zn_3O_{50.1}$ |
| V | $Mo_{12}Bi_1Fe_2Ni_6Tl_{0.25}P_{0.1}Zn_3O_{50.1}$ |
| VI | $Mo_{12}Bi_1Fe_2Ni_6Tl_{0.3}P_{0.1}Zn_3O_{50.2}$ |
| VII | $Mo_{12}Bi_1Fe_2Ni_6Tl_{1.0}P_{0.1}Zn_3O_{51.3}$ |
| VIII | $Mo_{12}Bi_1Fe_2Ni_6Tl_{1.5}P_{0.1}Zn_3O_{52.0}$ |

With the catalyst composition comprising said catalyst system, a mixture of propylene, air and steam in a molar ratio of 1 : 7 : 7 was contacted with said catalyst composition at a space velocity of 1,200 liter-gas/liter-catalyst/hour in the same manner as in Example 1.

The results are shown in the FIGURE of the attached drawing wherein the number of thallium atom (e) is indicated on the axis of the abscissa, the percent propylene conversion (%) is shown on the axis of the ordinate on the left side and the reaction temperature (°C.) is represented on the axis of the ordinate on the right side. The curves $a$, $b$, $c$, $d$ and $e$ represent respectively the conversion of propylene, the yield of acrolein, the reaction temperature, the yield of acrylic acid and the total yield of carbon monoxide an carbon dioxide.

From the FIGURE, it is shown that, although the catalyst composition No. I ($e = 0$) requires a temperature of 400° C. for attaining a conversion of propylene more than 95 %, an increase in the thallium content in the catalyst composition results in lowering the reaction temperature required for attaining the same result as above. The catalyst composition No. II ($e = 0.1$) shows a more than 95 percent conversion of propylene even at a temperature of 360° C. A higher increase in the thallium, however, requires a higher reaction temperature for attaining a conversion of propylene more than 95 percent. It is shown further that, when the catalyst compositions No. VII ($e = 1.0$) and No. VIII ($e = 1.5$) are used, the conversion of propylene is extremely decreased.

It can also be shown that the by-production of acrylic acid, carbon monoxide and carbon dioxide is contrary to the above results. Namely, the catalyst composition No. I ($e = 0$) affords acrylic acid in a 22 percent yield and carbon monoxide and carbon dioxide in a 9 percent total yield. The presence of thallium results in a remarkable decrease in these yields, and the catalyst composition No. VI ($e = 0.3$) allows a 7 percent yield of acrylic acid and a 3 percent total yield of carbon monoxide and carbon dioxide.

EXAMPLES 3 to 16

The process of Example 1 was repeated using the procedure and materials employed therein except for using various catalyst compositions and reaction conditions as presented in Table 1.

Table 1 also presents the results.

Table 1

| Example No. | Catalyst System | | | | | | | | | Reaction temperature (°C.) | Space velocity (l./l.hr.) | Propylene conversion (%) | Yields (%) | | | | Space time yield mole/l./hr. |
|---|---|---|---|---|---|---|---|---|---|---|---|---|---|---|---|---|---|
| | Mo | Bi | Fe | Ni | Tl | P | X | Y | O | | | | Acrolein | Acrylic acid | $CO_2$ | CO | |
| 3 | 12 | 1 | 2 | 6 | 0.3 | 0.1 | | $Ca_3$ | 50.2 | 325 | 1,200 | 90.1 | 78.7 | 7.0 | 2.0 | 1.4 | 2.81 |
| 4 | 12 | 1 | 2 | 6 | 0.3 | 0.1 | | $Sr_3$ | 50.2 | 375 | 1,200 | 93.4 | 74.7 | 11.3 | 2.8 | 2.5 | 2.67 |
| 5 | 12 | 1 | 2 | 7 | 0.1 | 0.1 | | $Cd_2$ | 49.9 | 337 | 1,200 | 95.2 | 80.7 | 8.3 | 3.0 | 1.7 | 2.88 |
| 6 | 12 | 1 | 2 | 6.5 | 0.1 | 0.1 | | $Sn_2$ | 51.4 | 365 | 1,200 | 95.5 | 82.7 | 8.0 | 1.8 | 1.0 | 2.96 |
| 7 | 12 | 1 | 2 | 6.5 | 0.1 | 0.1 | | $Pb_2$ | 49.4 | 350 | 1,200 | 93.7 | 76.6 | 11.0 | 3.0 | 2.3 | 2.74 |
| 8 | 12 | 1 | 2 | 6 | 0.1 | 0.1 | | $Ca_{1.5}Zn_{1.5}$ | 49.9 | 375 | 1,200 | 96.2 | 81.5 | 9.8 | 2.0 | 1.4 | 2.91 |
| 9 | 12 | 1 | 2 | 5 | 0.1 | 0.1 | $Mg_2$ | $Zn_2$ | 49.9 | 375 | 1,200 | 94.3 | 80.7 | 7.9 | 1.9 | 1.3 | 2.86 |

Table 1-continued

| Example No. | Catalyst System | | | | | | | | Reaction conditions | | Propylene conversion (%) | Yields (%) | | | | Space time yield mole/ l./hr.) |
|---|---|---|---|---|---|---|---|---|---|---|---|---|---|---|---|---|
| | Mo | Bi | Fe | Ni | Tl | P | X | Y | O | Reaction temperature (°C.) | Space velocity (l./hr.) | | Acrolein | Acrylic acid | $CO_2$ | CO | |
| 10 | 12 | 1 | 2 | 6 | 0.1 | 0.1 | | $Zn_{1.5}$ $Sn_{1.5}$ | 49.9 | 350 | 1,200 | 93.7 | 80.2 | 8.0 | 1.7 | 1.2 | 2.87 |
| 11 | 12 | 1 | 2 | 6 | 0.1 | 0.1 | $Mg_1$ | $Cu_1$ $Zn_1$ | 49.9 | 375 | 1,200 | 95.4 | 83.0 | 8.1 | 1.8 | 1.3 | 2.97 |
| 12 | 12 | 1 | 2 | 6 | 0.1 | 0.1 | $Co_1$ | $Cu_1$ $Zn_1$ | 49.9 | 375 | 1,200 | 96.2 | 82.8 | 8.8 | 1.6 | 1.2 | 2.96 |
| 13 | 12 | 1 | 2 | 6 | 0.1 | 0.1 | $Co_1$ | $Zn_1$ $Mg_1$ | 49.9 | 350 | 1,200 | 96.6 | 83.3 | 9.0 | 1.6 | 1.2 | 2.98 |
| 14 | 12 | 1 | 2 | 6 | 0.1 | 0.1 | $Mn_1$ | $Cu_1$ $Zn_1$ | 49.9 | 375 | 1,200 | 94.6 | 81.2 | 8.3 | 2.0 | 1.3 | 2.90 |
| 15 | 12 | 2 | 3 | 5 | 0.1 | 1 | | $Cd_2$ | 53.2 | 385 | 1,200 | 95.7 | 81.8 | 8.6 | 1.8 | 1.5 | 2.92 |
| 16 | 12 | 1 | 1 | 6.5 | 0.1 | 0.1 | | $Zn_2$ | 47.9 | 395 | 1,200 | 96.1 | 81.5 | 9.4 | 1.9 | 1.7 | 2.91 |

EXAMPLE 17

Using the catalyst composition of Example 1, the vapor phase oxidation of propylene to acrolein was carried out continuously in the same manner as in Example 1 except for using the space velocity of 400 liter-gas/liter-catalyst/hour and the reaction temperature of 315° C. instead. The following results were obtained: propylene conversion, 96.9 percent; acrolein yield, 82.3 percent; acrylic acid yield, 8.1 percent.

EXAMPLE 18

Using the catalyst composition of Example 1, the vapor phase oxidation of propylene to acrolein was carried out continuously under the same reaction conditions as in Example 1 except for using the space velocity of 3,600 liter-gas/liter-catalyst/hour and the reaction temperature of 400° C. instead. The following results were obtained: propylene conversion, 92.3 percent; acrolein yield, 74.5 percent; acrylic acid yield, 10.3 percent; space time yield of acrolein, 7.99 mol/liter-catalyst/hour.

EXAMPLE 19

Using the catalyst composition obtained in Example 5, the vapor phase oxidation of propylene to acrolein was carried out continuously. The reaction conditions were the same as in Example 1, but the space velocity was 7,200 liter-gas/liter-catalyst/hour and the reaction temperature was 400° C. instead. The following results were obtained: propylene conversion, 92.0 percent; acrolein yield, 72.4 percent; acrylic acid yield, 9.0 percent; space time yield of acrolein, 15.1 mol/liter-catalyst/hour.

EXAMPLE 20

Using the catalyst composition of Example 1, the vapor phase oxidation of propylene to acrolein was carried out continuously for 960 hours under the same reaction conditions as in Example 1. The following results were obtained: propylene conversion, 93.1 percent; acrolein yield, 81.5 percent; acrylic acid yield, 7.0 percent.

EXAMPLE 21

The catalyst composition of Example 5 was used to carry out the continuous vapor phase oxidation of propylene to acrolein for 960 hours under the same reaction condition as in Example 4. The following results were obtained: propylene conversion, 93.7 percent; acrolein yield, 77.5 percent; acrylic acid yield, 9.4 percent.

EXAMPLES 22 to 39

The catalyst compositions were prepared using the procedure used in Example 1 and employed to carry out the vapor phase oxidation in the same manner as in Example 1 except for using reaction temperatures as presented in Table 2.

Table 2 presents the composition of catalysts, reaction conditions and reaction results.

Table 2

| Example No. | Catalyst System | | | | | | | | | Reaction temperature (°C.) | Propylene conversion (%) | Yields (%) | | | | Space time yield mole/ l./hr.) |
|---|---|---|---|---|---|---|---|---|---|---|---|---|---|---|---|---|
| | Mo | Bi | Fe | Ni | Tl | P | X | Y | O | | | Acrolein | Acrylic acid | $CO_2$ | CO | |
| 22 | 12 | 1 | 4 | 6 | 0.2 | 0.1 | | $Zn_3$ | 53.1 | 375 | 94.8 | 80.0 | 7.8 | 2.0 | 1.0 | 2.86 |
| 23 | 12 | 1 | 7.5 | 6 | 0.4 | 0.1 | | $Zn_3$ | 58.6 | 400 | 94.7 | 77.8 | 8.5 | 3.6 | 2.6 | 2.78 |
| 24 | 12 | 1 | 2 | 6 | 0.3 | 0.1 | $Mg_{1.5}$ | $Zn_{1.5}$ | 50.2 | 375 | 95.9 | 84.2 | | | | 3.01 |
| 25 | 12 | 1 | 2 | 6 | 0.2 | 0.2 | | $Zn_3$ | 52.3 | 375 | 95.6 | 81.6 | | | | 2.92 |
| 26 | 12 | 3 | 2 | 4 | 0.1 | 0.2 | $Mg_3$ $Co_3$ | $Zn_3$ | 57.15 | 375 | 92.4 | 81.7 | | | | 2.92 |
| 27 | 12 | 1 | 2 | 9 | 0.2 | 0.2 | | $Zn_{0.5}$ | 50.8 | 375 | 96.8 | 83.9 | | | | 3.00 |
| 28 | 12 | 0.1 | 2 | 5 | 0.2 | 0.2 | $Co_1$ | $Zn_3$ | 48.95 | 400 | 93.8 | 80.1 | 8.8 | 1.8 | 1.1 | 2.86 |
| 29 | 12 | 1 | 0.1 | 5 | 0.2 | 0.2 | $Co_1$ | $Zn_3$ | 47.45 | 425 | 94.3 | 78.4 | 8.9 | 3.2 | 2.5 | 2.80 |
| 30 | 12 | 0.2 | 0.3 | 8 | 0.2 | 0.2 | | $Zn_2$ | 47.55 | 425 | 95.1 | 81.2 | 9.0 | 1.9 | 1.1 | 2.90 |
| 31 | 12 | 1 | 2 | 3 | 0.2 | 0.2 | $Co_3$ | $Zn_6$ | 53.30 | 400 | 92.3 | 77.6 | 8.5 | 2.9 | 2.3 | 2.77 |
| 32 | 12 | 1 | 0.5 | 12 | 0.2 | 0.3 | | $Zn_{0.1}$ | 51.40 | 375 | 93.5 | 80.9 | 8.2 | 2.1 | 1.4 | 2.89 |
| 33 | 12 | 1 | 2 | 0.1 | 0.2 | 0.2 | $Co_9$ | $Zn_{0.1}$ | 50.50 | 400 | 94.9 | 79.5 | 8.7 | 2.8 | 2.0 | 2.84 |
| 34 | 12 | 1 | 2 | 6 | 0.2 | 0 | | $Zn_3$ | 49.80 | 375 | 95.7 | 81.9 | 8.0 | 2.0 | 1.2 | 2.93 |
| 35 | 12 | 1 | 2 | 6 | 0.2 | 2 | | $Zn_3$ | 54.80 | 400 | 94.2 | 79.1 | 9.1 | 2.3 | 1.6 | 2.83 |

Table 2-continued

| Example No. | Catalyst System | | | | | | | | Reaction temperature (°C.) | Propylene conversion (%) | Yields (%) | | | | Space time yield mole/ l./hr.) |
|---|---|---|---|---|---|---|---|---|---|---|---|---|---|---|---|
| | Mo | Bi | Fe | Ni | Tl | P | X | Y | O | | Acrolein | Acrylic acid | CO$_2$ | CO | |
| 36 | 12 | 1 | 2 | 6 | 0.05 | 0.2 | | Zn$_3$ | 50.08 | 375 | 96.2 | 82.2 | 9.6 | 1.5 | 1.3 | 2.94 |
| 37 | 12 | 5 | 2 | 4 | 0.1 | 0.2 | | Zn$_2$ | 53.15 | 425 | 93.1 | 75.4 | 6.9 | 4.8 | 3.3 | 2.69 |
| 38 | 12 | 2.5 | 7.5 | 6 | 1 | 2 | Co$_3$ | Zn$_3$ | 69.50 | 425 | 94.0 | 72.8 | 5.5 | 7.5 | 6.9 | 2.60 |
| 39 | 12 | 0.2 | 0.3 | 3 | 0.05 | 0 | Co$_{1.5}$ | Zn$_{1.5}$ | 42.83 | 425 | 95.5 | 76.8 | 7.4 | 5.2 | 4.0 | 2.74 |

EXAMPLE 40

The catalyst composition obtained in Example 24 was used to carry out a 50-day continuous vapor phase oxidation of propylene to acrolein in the same manner as in Example 1 except for using the reaction temperature of 375° C. instead. This continuous reaction did not cause any deterioration of its catalytic activity and provided a propylene conversion of 93.6 percent, an acrolein selectivity of 90.3 percent, and an acrolein yield of 84.5 percent.

EXAMPLE 41

With the catalyst composition No. IV obtained in Example 2, the vapor phase oxidation was carried out by passing a gaseous mixture of propylene and air in the propylene to air mole ratio of 1 : 7 in the absence of steam under the same conditions as in Example 1 except for using a space velocity of 640 liter-gas/liter-catalyst/hour instead of 1,200. The results were: propylene conversion, 87.5 percent; acrolein yield 77.3 percent.

EXAMPLE 42

The catalyst composition No. IV of Example 2 was employed to carry out the vapor phase oxidation in the same manner as in Example 1 except that a gaseous mixture of propylene, air and steam in the propylene to air to steam mole ratio of 1 : 5 : 5.3 was passed thereover at a temperature of 375° C. The results obtained were: propylene conversion, 92.8 percent; acrolein yield, 80.5 percent.

EXAMPLE 43

The catalyst composition No. IV of Example 2 was used to carry out the vapor phase oxidation in the same manner as in Example 1 except that a gaseous mixture of propylene, air and steam in the propylene to air to steam mole ratio of 1 : 30 : 30 was passed thereover at a temperature of 375° C. The results obtained were a propylene conversion of 95.5 percent and an acrolein yield of 84.2 percent.

EXAMPLE 44

The catalyst composition No. IV of Example 2 was employed to carry out the vapor phase oxidation in the same manner as in Example 1 in which, however, a gaseous mixture of propylene, air and steam in the propylene to air to steam mole ratio of 1 : 2.5 : 12 was fed at a space velocity of 6,000 liter-gas/liter-catalyst/-hour and the reaction was carried out at a temperature of 400°C. The results obtained were a propylene conversion of 48.9 percent, an acrolein selectivity of 98.5 percent, an acrolein yield of 48.2 percent, a space time yield of 8.33 mole/liter-catalyst/hour and an oxygen reactivity of 98.9 percent.

REFERENCE EXAMPLE 1

The procedure employed in Example 1 was repeated to give a catalyst composition of the formula:

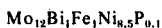

$$Mo_{12}Bi_1Fe_1Ni_{8.5}P_{0.1}$$

(wherein the carrier component is omitted).

Using this catalyst composition, the vapor phase oxidation of propylene to acrolein was carried out continuously as in Example 1 except for using the reaction temperature of 400°C. instead. The following results were obtained: propylene conversion, 90.9 percent; acrolein yield, 52.6 percent; acrylic acid yield, 21.5 percent; carbon dioxide yield, 6.8 percent; carbon monoxide yield, 5.3 percent; space time yield of acrolein, 1.88 mol/liter-catalyst/hour.

REFERENCE EXAMPLE 2

The procedure employed in Example 1 was repeated to give a catalyst composition of the formula:

$$Mo_{12}Bi_1Fe_1Ni_{4.5}Co_4P_{0.08}O_{47.7}$$

(wherein the carrier component is omitted).

The catalyst composition was employed to conduct the vapor phase oxidation of propylene to acrolein continuously in the same manner as in Example 1 except for using the reaction temperature of 400° C. instead. The following results were obtained: propylene conversion, 90.7 percent; acrolein yield, 64.2 percent; acrylic acid yield, 18.1 percent; carbon dioxide yield, 4.2 percent; carbon monoxide yield, 1.8 percent; space time yield of acrolein, 2.29 mole/liter-catalyst/hour.

REFERENCE EXAMPLE 3

The process of Example 1 was repeated using the procedure employed therein to give a catalyst composition of the formula:

$$Mo_{12}Bi_1Fe_1Ni_{8.5}Tl_{0.2}P_{0.1}O_{48.1}$$

(wherein the carrier component is omitted).

With this catalyst composition, the vapor phase oxidation of propylene to acrolein was carried out continuously in the same manner as in Example 1 except for using the reaction temperature of 375° C. instead. The following results were obtained: propylene conversion, 96.1 percent; acrolein yield, 78.4 percent; acrylic acid yield, 9.8 percent.

REFERENCE EXAMPLES 4 to 10

The process of Example 1 was repeated using the procedure used therein to give various catalyst compositions as presented in the following table. These catalyst compositions were then used to carry out the vapor phase oxidation of propylene to acrolein in the same manner as in Example 1. The results are shown in Table 3.

REFERENCE EXAMPLE 11

The process of Example 1 was repeated using the procedure used therein to give a catalyst composition of the formula:

$$Mo_{12}Bi_1Fe_2Ni_{6.5}Tl_{1.5}P_{0.1}Zn_2O_{51.5}$$

(wherein the carrier component is omitted).

This catalyst composition was used to conduct the vapor phase oxidation of propylene to acrolein continuously as in Example 1 except for using the reaction temperature of 450° C. instead. The following results were obtained: propylene conversion, 55.1 percent; acrolein yield, 27.9 percent.

REFERENCE EXAMPLE 12

Using the catalyst composition obtained in Reference Example 1, the vapor phase oxidation of propylene to acrolein was carried out continuously for 120 hours in the same manner as in Reference Example 1. The following results were obtained: propylene conversion 78.3 percent; acrolein yield, 33.7 percent, acrylic acid yield, 23.9 percent.

REFERENCE EXAMPLE 13

The catalyst composition of Reference Example 3 was used to carry out the vapor phase oxidation of propylene to acrolein continuously for 480 hours in the same manner as in Reference Example 3. The following results were obtained: propylene conversion, 88.4 percent; acrolein yield, 68.1 percent; acrylic acid yield, 12.1 percent.

REFERENCE EXAMPLE 14

The process of Example 23 was repeated using the procedure used therein to give a catalyst composition of the formula:

$$Mo_{12}Bi_1Fe_{7.5}Ni_6P_{0.1}Zn_3O_{58}$$

(wherein the carrier component is omitted).

With this catalyst composition, the vapor phase oxidation of propylene to acrolein was carried out continuously as in Example 23. The following results were obtained: propylene conversion, 74.8 percent; acrolein yield, 43.2 percent; acrylic acid yield, 6.3 percent; carbon dioxide yield, 15.1 percent; carbon monoxide yield, 5.4 percent; acetaldehyde yield, 3.2 percent.

What we claim is:

1. A process for preparing acrolein by the vapor phase oxidation of propylene which comprises contacting propylene and oxygen at a temperature of from 200° to 550° C., a pressure of from 0.7 to 5 absolute atmospheres and a space velocity of 100 to 24,000 liter-gas/liter-catalyst/hour in a mole ratio of propylene to oxygen of 1 : 0.4 to 1 : 3 in the presence of a catalyst composition consisting essentially of a catalyst system of the formula:

$$Mo_aBi_bFe_cNi_dTl_eP_fX_gY_hO_i$$

wherein X is at least one member selected from the group consisting of Mg, Mn and Co, Y is at least one member selected from the group consisting of Cu, Ca, Sr, Zn, Cd, Sn and Pb and $a$, $b$, $c$, $d$, $e$, $f$, $g$, $h$ and $i$ represent respectively the number of atoms and $a$ is 12, $b$ is from 0.1 to 5, $c$ is from 0.1 to 12, $d$ is from 0.1 to 12, $e$ is 1 or less but not 0, $f$ is from 0 to 5, $g$ is from 0 to 12, $h$ is from 0.1 to 12 and $i$ is a number determined by the valence requirements of the other atoms present, provided that the sum of $b$ plus $c$ is from 0.2 to 12.5 and the sum of $d$ plus $g$ plus $h$ is from 0.2 to 27.

2. The process of claim 1 wherein $a$ is 12, $b$ is from 0.1 to 5, $c$ is from 0.1 to 7.5, $d$ is from 0.1 to 12, $e$ is from 0.05 to 1, $f$ is up to 2, $g$ is up to 9, $h$ is from 0.1 to 6 and $i$ is from 36.4 to 77.0.

3. The process of claim 1 wherein $a$ is 12, $b$ is from 0.1 to 5, $c$ is from 0.1 to 7.5, $d$ is from 0.1 to 12, $e$ is from 0.05 to 1, $f$ is up to 2, $g$ is up to 9, $h$ is from 0.1 to 6 and $i$ is 42.8 to 70.5, provided that the sum of $b$ plus $c$ is from 0.5 to 10 and the sum of $d$ plus $g$ plus $h$ is from 6 to 13.

4. The process of claim 1 wherein X is one or two members selected from the group consisting of Mg, Mn and Co.

5. The process of claim 1 wherein Y is one or two members selected from the group consisting of Cu, Ca, Sr, Zn, Cd, Sn and Pb.

6. The process of claim 5 wherein Y is one or two members selected from the group consisting of Cu, Zn, Cd and Sn.

7. The process of claim 5 wherein Y is Zn.

8. The process of claim 1 wherein the catalyst composition consists essentially of said catalyst system.

9. The process of claim 1 wherein the reaction is carried out at a temperature of from 250° to 500° C.

10. The process of claim 9 wherein the temperature is from 300° to 450° C.

Table 3

| Reference Example No. | Catalyst System | | | | | | | Reaction conditions | | Propylene conversion (%) | Yields (%) | | | | | Space time yield mole/ l./hr. |
|---|---|---|---|---|---|---|---|---|---|---|---|---|---|---|---|---|
| | Mo | Bi | Fe | Ni | P | X | Y | O | Reaction temperature (°C.) | Space velocity (l./l.hr.) | | Acrolein | Acrylic acid | $CO_2$ | CO | Acetaldehyde | |
| 4 | 12 | 1 | 2 | 6.5 | 0.1 | | $Zn_2$ | 49.3 | 375 | 1,200 | 91.9 | 60.7 | 18.1 | 4.1 | 3.3 | 5.2 | 2.17 |
| 5 | 12 | 1 | 2 | 6 | 0.1 | | $Ca_3$ | 49.8 | 400 | 1,200 | 84.8 | 47.6 | 12.5 | 8.6 | 7.6 | 4.8 | 1.70 |
| 6 | 12 | 1 | 2 | 6 | 0.1 | | $Sr_3$ | 49.8 | 400 | 1,200 | 74.7 | 38.6 | 11.2 | 9.8 | 8.8 | 4.3 | 1.38 |
| 7 | 12 | 1 | 2 | 7 | 0.1 | | $Cd_2$ | 49.8 | 400 | 1,200 | 81.7 | 48.4 | 10.6 | 8.4 | 6.7 | 5.0 | 1.73 |
| 8 | 12 | 1 | 2 | 6.5 | 0.1 | | $Pb_2$ | 49.3 | 400 | 1,200 | 84.0 | 52.0 | 9.5 | 8.5 | 5.7 | 5.1 | 1.86 |
| 9 | 12 | 1 | 2 | 6 | 0.1 | | $Zn_1 Cd_1 Sn_1$ | 49.8 | 400 | 1,200 | 92.4 | 57.1 | 20.4 | 5.3 | 4.3 | 4.3 | 2.04 |
| 10 | 12 | 1 | 2 | 6 | 0.1 | $Mg_1$ | $Cu_1$ | 49.8 | 400 | 1,200 | 90.3 | 59.4 | 17.5 | 4.8 | 3.9 | 3.8 | 2.12 |

11. The process of claim 1 wherein the reaction is carried out at a space velocity of from 200 to 12,000 liter-gas/liter-catalyst/hour.

12. The process of claim 11 wherein the reaction is carried out at a space velocity of 300 to 8,000 liter-gas/liter-catalyst/hour.

13. The process of claim 1 wherein the mole ratio of propylene to oxygen is from 1 : 0.4 to 1 : 3.

14. The process of claim 1 wherein the reaction is carried out in the presence of steam.

15. The process of claim 14 wherein the steam is mixed with a mixture of propylene and oxygen.

16. The process of claim 15 wherein the mole ratio of steam to oxygen is from 1 : 1 to 15 : 1.

* * * * *